(12) United States Patent
Patel

(10) Patent No.: US 11,478,338 B1
(45) Date of Patent: Oct. 25, 2022

(54) SOLID DIAMOND DENTAL IMPLANT, COMPOSITION AND METHOD

(71) Applicant: Sachin Patel, Chicago, IL (US)

(72) Inventor: Sachin Patel, Chicago, IL (US)

( * ) Notice: Subject to any disclaimer, the term of this patent is extended or adjusted under 35 U.S.C. 154(b) by 45 days.

(21) Appl. No.: 17/317,964

(22) Filed: May 12, 2021

(51) Int. Cl.
*A61C 8/00* (2006.01)

(52) U.S. Cl.
CPC .................................. *A61C 8/0012* (2013.01)

(58) Field of Classification Search
CPC ... A61C 8/00–0098; A61C 7/02; A61C 7/023; A61F 2310/00005; A61F 2310/00167; A61F 2013/53734; A61F 2013/53739; A61F 2013/530124
See application file for complete search history.

(56) References Cited

U.S. PATENT DOCUMENTS

| | | | |
|---|---|---|---|
| 6,447,295 B1 | 9/2002 | Kumar et al. | |
| 2003/0074051 A1* | 4/2003 | Freislinger Luehrs | A61F 2/915 623/1.15 |
| 2009/0075236 A1 | 3/2009 | Towse et al. | |
| 2014/0272794 A1 | 9/2014 | Legum | |
| 2015/0282907 A1* | 10/2015 | Zipprich | A61C 8/0093 433/32 |
| 2022/0015873 A1* | 1/2022 | Tomasik | C30B 29/04 |

FOREIGN PATENT DOCUMENTS

| | | |
|---|---|---|
| CN | 105411695 A | 3/2016 |
| CN | 209734190 U | 12/2019 |
| CN | 209734191 U | 12/2019 |
| CN | 111839770 A | 10/2020 |
| EP | 0534078 A1 | 3/1993 |
| JP | 6029865 B2 | 11/2016 |
| RU | 2571559 C1 | 12/2015 |
| RU | 185777 U1 | 12/2018 |

OTHER PUBLICATIONS

Kim, SK et al. An Abutment Screw Loosening Study of a Diamond Like Carbon-coated Cp Titanium Implant, 2005, Journal of Oral Rehabilitation 32(5): 346-350.

Lepesqueur, LS et al., Coating Dental Implant Abutment Screws With Diamondlike Carbon Doped With Diamond Nanoparticles: the Effect on Maintaining Torque After Mechanical Cycling, 2015, International Journal of Oral & Maxillofacial Implants 30(6): 1310-1316.

Metzler et al., Nano-crystalline Diamond-coated Titanium Dental Implants—a Histomorphometric Study in Adult Domestic Pigs, 2012, Journal of Cranio-Maxillofacial Surgery 41(6): 532-538.

* cited by examiner

*Primary Examiner* — Yogesh P Patel
(74) *Attorney, Agent, or Firm* — Lesley A. Wallerstein, LLC

(57) ABSTRACT

Pure compressed diamond (PCD), grown in a laboratory, is laser-shaped into dental implants with high tensile strength, high compressive strength, high thermal conductivity, and which are harder than any other substance on earth. PCD is harder than ceramic zirconia and harder than titanium. Because PCD is pure carbon, it is also 100% compatible with carbon-based living tissue. Unlike titanium, it does not provoke an immune response. PCD implants readily integrate into human jawbone. This drastically reduces post-surgery bone loss.

7 Claims, No Drawings

SOLID DIAMOND DENTAL IMPLANT, COMPOSITION AND METHOD

FIELD OF THE INVENTION

This invention relates to the field of reconstructive dentistry, specifically improvements to dental implant compositions and methods of replacing diseased and damaged teeth.

BACKGROUND OF THE INVENTION

Teeth are among the hardest parts of the human body. They must bite, tear, grind and otherwise break down food for a lifetime. Like all living tissue, teeth are nonetheless vulnerable to decay, to disease, and to injury. Teeth are anchored into the jawbone, also living tissue. Removing and replacing teeth requires painstaking, and painful, surgery. The most permanent solution is an implant.

Prosthetic teeth consist of three general parts: an implant, an abutment and a crown. What we call the implant itself is a rigid and threaded fastener that fills the space where a root once was. It sits beneath the gumline and is not visible. A top side of the implant contains a hole configured to receive a post called an abutment. The abutment is visible above the gumline until a crown is attached thereonto.

Traditionally, dental implants comprise titanium or ceramic zirconia. These materials resist fracture, are chemically inert, unlikely to be rejected, and integrate readily into the jawbone. As well-tolerated and durable as these materials have proven, I have discovered an even harder, an even more unreactive, even more biocompatible, even more osseointegrative material for dental implants: pure compressed diamond.

BRIEF SUMMARY OF THE INVENTION

Pure compressed diamond (PCD), grown in a laboratory, is laser-shaped into dental implants with high tensile strength, high compressive strength, high thermal conductivity, and which are harder than any other substance on earth. PCD is harder than ceramic zirconia and harder than titanium. Because PCD is pure carbon, it is also 100% compatible with carbon-based living tissue. Unlike titanium, it does not provoke an immune response. PCD implants readily integrate into human jawbone. This drastically reduces post-surgery bone loss.

DETAILED DESCRIPTION OF THE INVENTION

Growing and shaping pure diamond in the laboratory is well known. There are two main ways to synthesize diamonds, either of which can create the implant. One way to grow a diamond is to place a tiny diamond crystal in a small capsule. We place the capsule in a high-temperature, high-pressure chamber and combine it with carbon dust. We heat and pressurize it for several weeks. This mimics how natural diamonds are made deep within the earth, only on a much faster scale.

Another way to grow diamonds is to shave a thin slice, called a "seed," off an existing diamond. We lay several of these seeds into a cavity in a chemical vapor deposition (CVD) machine. We remove the air, crank up the heat, pump in methane gas and hit the gas with a beam of microwave energy. The extreme heat vaporizes the methane into its constituent elements carbon and hydrogen. The free carbon is attracted to, then bonds to, the flat surfaces of the seeds. The CVD machine runs for a few weeks, continuing to deposit carbon onto the seed. Eventually enough carbon bonds to the seed to form a rough diamond crystal. We prefer using CVD-grown diamonds because they are clearer, more evenly colored, and are more flawlessly crystallized. Diamonds chosen for dental implants will have the highest clarity; preferably graded at least VVS (very very slight inclusions) and most preferably graded at least IF (internally flawless) on the Gemological Institute of America scale. VVS graded diamonds have minute inclusions that are difficult for a skilled grader to see under 10× magnification. The VVS category is divided into two grades; VVS1 denotes a higher clarity grade than VVS2. Pinpoints and needles set the grade at VVS. IF diamonds have no inclusions visible under 10× magnification, only small blemishes on the diamond surface.

The rough diamond crystal is shaped by laser into the desired implant shape. Preferably we use Nd: YAG (neodymium-doped yttrium aluminum garnet) lasers. The implant will be generally conical and longitudinal in shape, with a wider top configured for coupling to an abutment piece, a narrower, pointed, bottom configured for installing into jawbone, and a side body. With the laser, we create in the top a hole dimensioned to snugly receive a male part of a conventional abutment. Preferably, the hole is a regular 2.42 hexagon, but other hole shapes and other abutment coupling means are possible while remaining within the scope of this invention. The bottom of the implant is pointed.

Into the side body of the implant, we create with the laser downward angled threads. These threads allow the implant to be driven into bone and prevent the implant from slipping out of position. Preferably the threads will spiral clockwise at between 65-90 degrees to the vertical. Preferably there will be 2-3 mm of vertical space between threads, but other dimensions and proportions are possible while remaining within the scope of this invention.

The jawbone is prepared to receive the diamond implant in the same manner as for titanium or ceramic zirconia. We prefer the method taught by Dr. Salah Huwais known as "Osseodensification." Special drilling burs called the Versah Densah burs have a blunt cutting edge. We rotate and drill the bur in a counterclockwise direction. This bur and method of drilling actually expand and preserve bone, rather than cut and destroy it. We collect the bone removed during the primary osteotomy and preserve it for autogenous bone grafting during and after implant placement and closure. This further facilitates osseointegration and healing.

The diamond implant is screwed into the jawbone pointed side into the bone and hole side away from the bone. The abutment is coupled to the implant and the crown is affixed to the abutment. Gum tissue is allowed to heal.

Although embodiments and examples of the invention have been shown and described, it is to be understood that various modifications, substitutions, and rearrangements of parts, components, steps, as well as other uses, shapes, construction, and design of this composition and method can be made by those skilled in the art without departing from the novel spirit and scope of this invention.

I claim:

1. An endosseous dental implant consisting essentially of pure compressed diamond.

2. The endosseous dental implant of claim 1, wherein the pure compressed diamond has a clarity grade of at least VVS.

3. The endosseous dental implant of claim 2, wherein the pure compressed diamond has a clarity grade of at least IF.

4. The endosseous dental implant of claim 1, wherein the implant is generally conical in shape, having a wider top end, a pointed bottom end, and a sidewall.

5. The endosseous dental implant of claim 4, wherein the top end further comprises a hole dimensioned to snugly receive an abutment, the bottom end is tapered to a point and the sidewall is threaded.

6. A method of preventing bone loss, peri-implantitis and peri-implant mucositis in a patient's jawbone, comprising implanting a dental implant consisting essentially of pure compressed diamond into a patient's jawbone.

7. A method of replacing a tooth, comprising implanting an endosseous dental implant consisting essentially of pure compressed diamond into a patient's jawbone.

* * * * *